US00PP28483P3

(12) United States Plant Patent
Suphachadiwong

(10) Patent No.: US PP28,483 P3
(45) Date of Patent: Oct. 3, 2017

(54) ***VANDA* PLANT NAMED 'SPCDW1409'**

(50) Latin Name: ***Vanda* spp.**
Varietal Denomination: SPCDW1409

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 49 days.

(21) Appl. No.: 14/757,634

(22) Filed: Dec. 23, 2015

(65) Prior Publication Data

US 2016/0192569 P1 Jun. 30, 2016

(30) Foreign Application Priority Data

Dec. 30, 2014 (QZ) ..... 2014/3622

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1409' which is characterized by sepals and petals with a unique violet color, overlaid with a color pattern consisting of dark violet slight tessellation, dark violet irregular blurs and distinct spots, as well as a very dark purple labellum contrasting the petals and sepals, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1409'.

CROSS REFERENCE TO RELATED APPLICATIONS

This application claims priority to the Community Plant Variety Rights application number 2014/3622, filed Dec. 30, 2014, which is herein incorporated by reference.

BACKGROUND OF THE INVENTION

Parentage: The *Vanda* variety 'SPCDW1409' is the result of a planned breeding program. The new variety originated as a seedling from the crossing of the unpatented, proprietary seed parent *Vanda* 'F211' with the unpatented, proprietary pollen parent *Vanda* 'JBL211'. Both parents were developed by, and are owned by, the inventor and were never commercially released. The crossing was made by the inventor in his research greenhouse in Bangphra, Thailand in December of 1986.

The new variety was first selected in February of 1991, in a research greenhouse in Bangphra, Thailand belonging to the inventor. After identifying the new variety as a potentially interesting selection, the inventor continued confidential testing and propagation of 'SPCDW1409', assessing stability of the unique characteristics of this variety.

Asexual Reproduction: Asexual reproduction of the new cultivar 'SPCDW1409', by way of mericloning, was first initiated in October of 2009 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1409' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1409'. These characteristics in combination distinguish 'SPCDW1409' as a new and distinct *Vanda* cultivar:

1. *Vanda* 'SPCDW1409' exhibits sepals and petals with a unique purple color; and
2. *Vanda* 'SPCDW1409' exhibits sepals and petals overlaid with a color pattern consisting of dark purple slight tessellation, dark purple irregular blurs, and distinct dark purple spots; and
3. *Vanda* 'SPCDW1409' exhibits a very dark purple general tonality of the labellum which contrasts the lighter purple petals and sepals.

BOTANICAL DESCRIPTION OF THE PLANT

Figure 1:
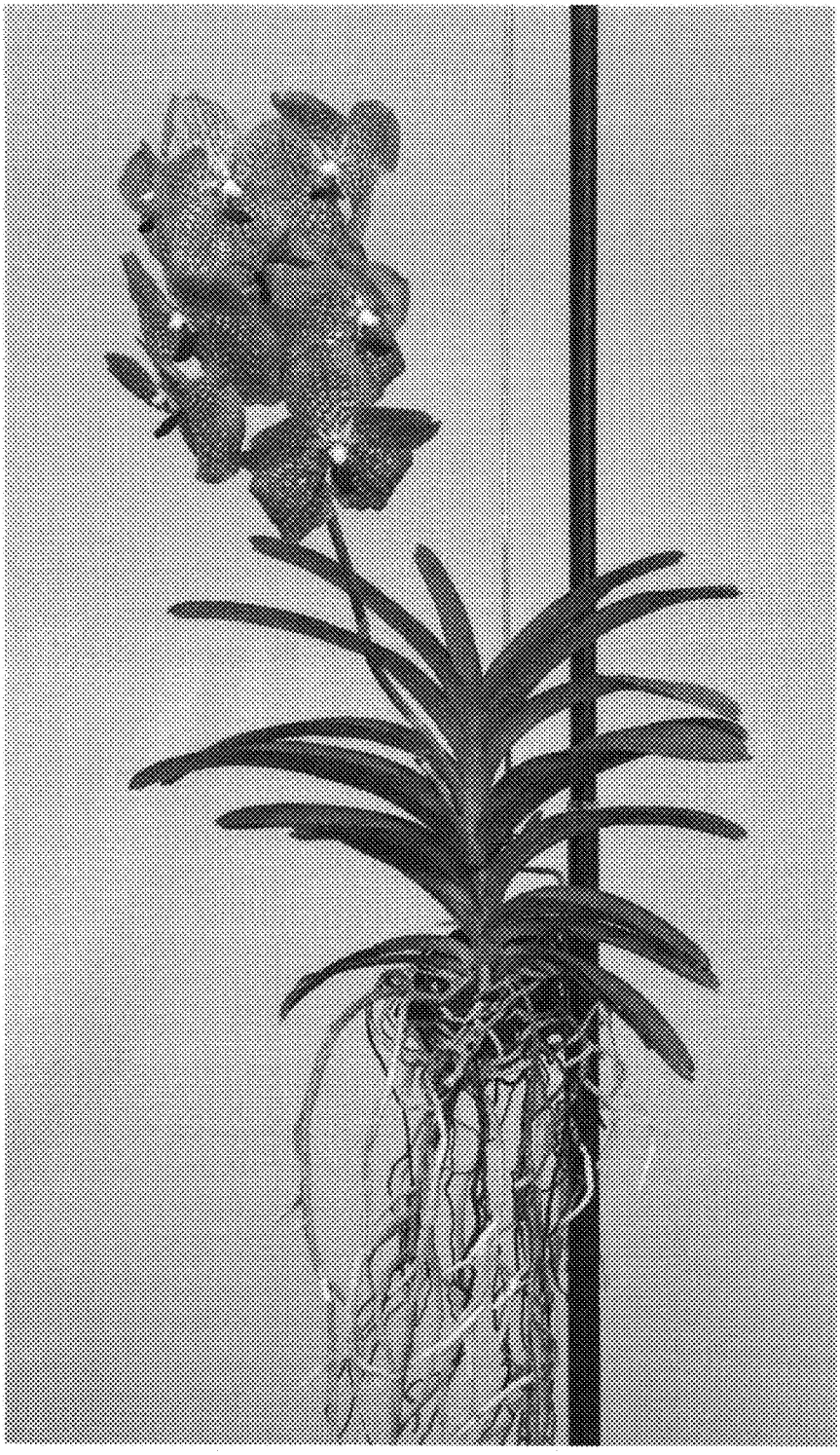
FIG. 1 illustrates, as nearly true as it is reasonably possible to make the same in color photographs of this type, an exemplary plant of 'SPCDW1409' grown in a commercial greenhouse in Honselersdijk, the Netherlands. This plant is approximately 6 years old from the time of mericloning, shown planted in an 8 by 8 cm container.
Figure 2:
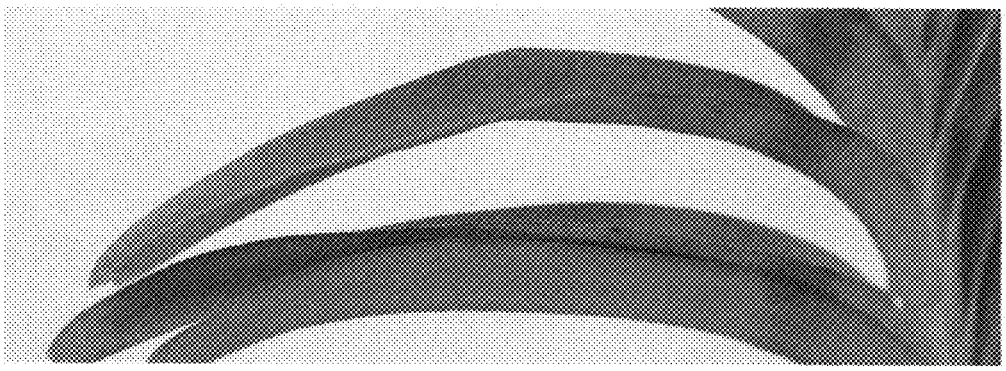
FIG. 2 illustrates, as nearly true as it is reasonably possible to make the same in color photographs of this type, the typical foliage of 'SPCDW1409'.
Figure 3:
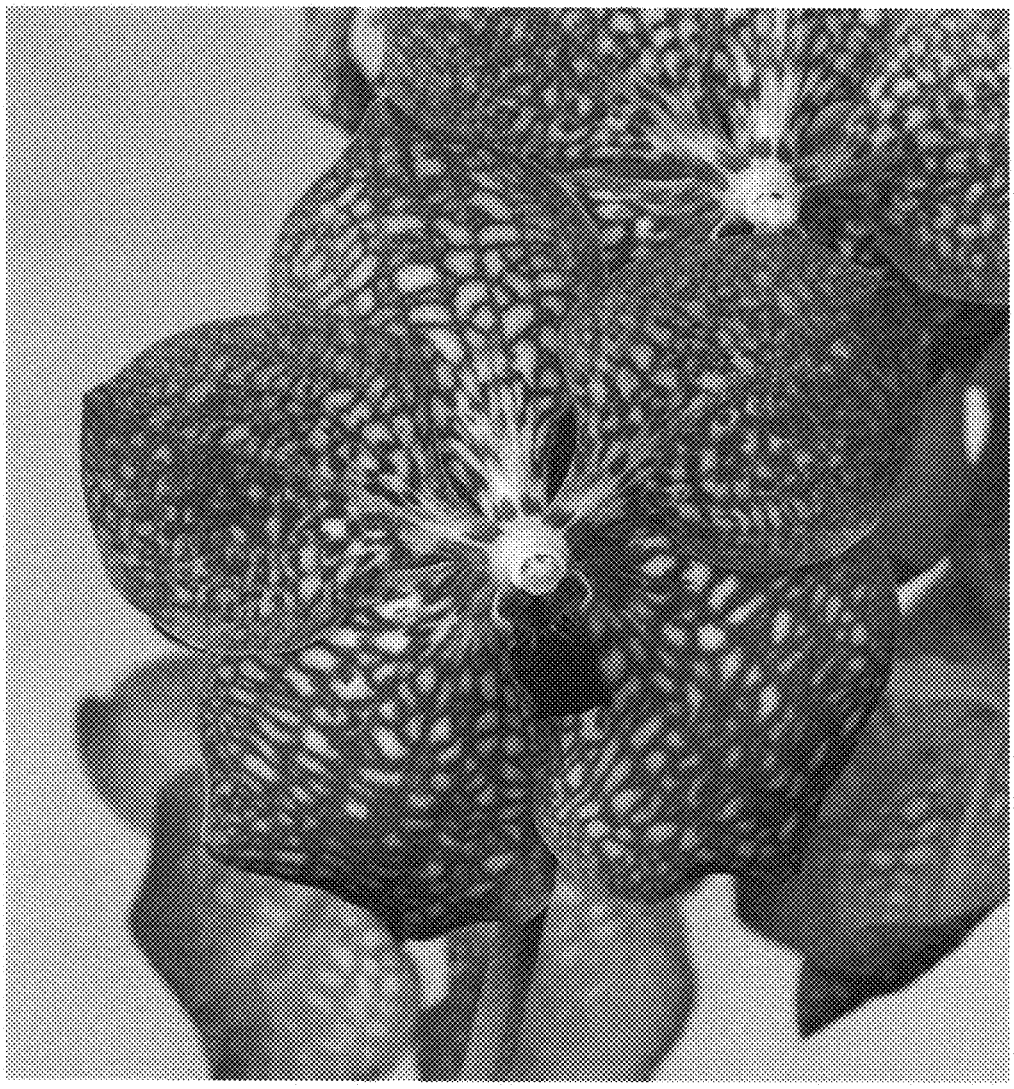
FIG. 3 illustrates, as nearly true as it is reasonably possible to make the same in color photographs of this type, the typical flower of 'SPCDW1409'.
Figure 4:
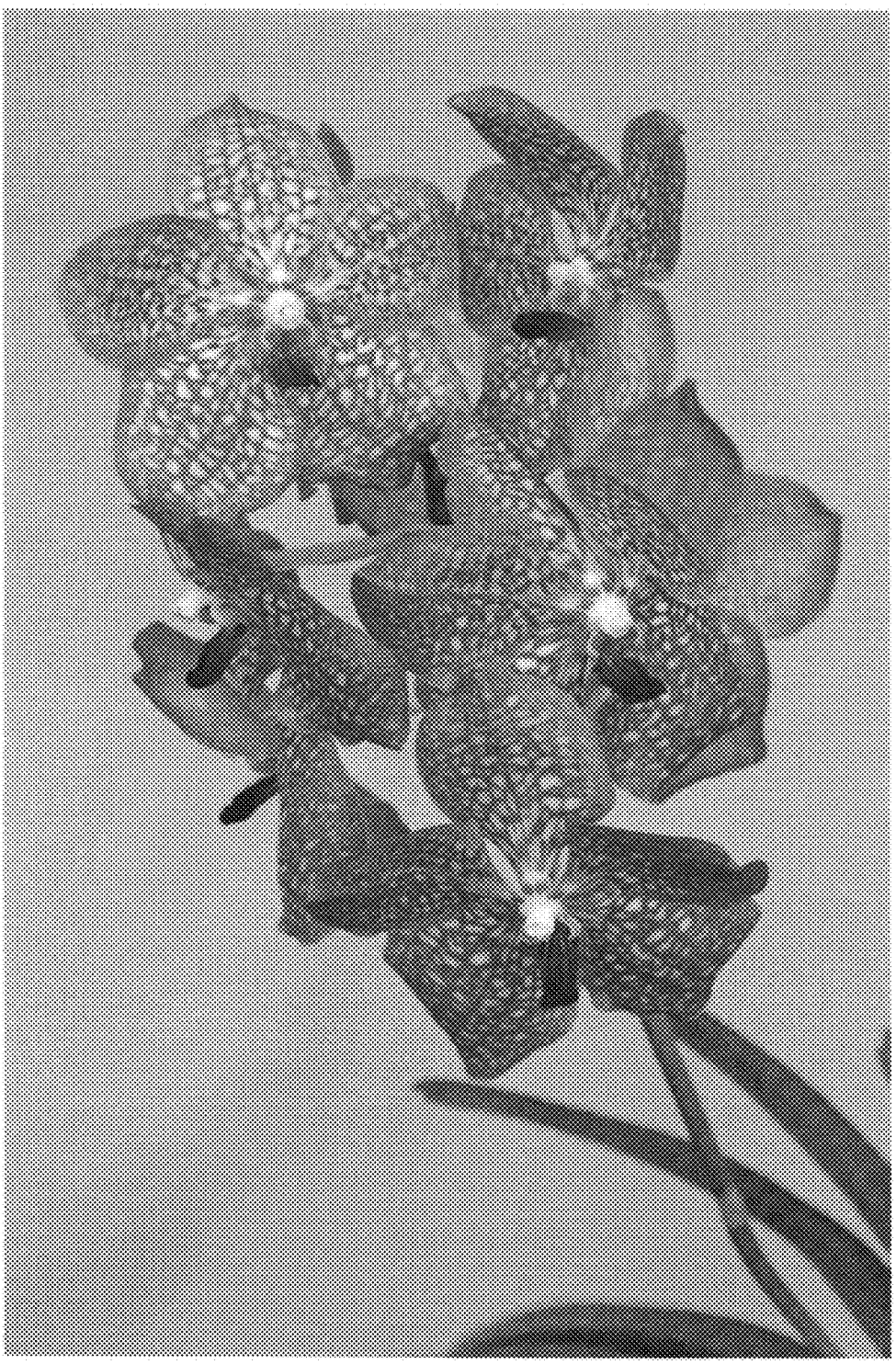
FIG. 4 illustrates, as nearly true as it is reasonably possible to make the same in color photographs of this type, the typical inflorescence of 'SPCDW1409'.

The following observations and measurements made in December of 2015 describe averages from a sample set of six specimens of six year-old 'SPCDW1409' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1409' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1409' and comparisons with other varieties of *Vanda* are provided below.

Plant description:

- *Growth habit*.—Perennial; monopodial, upright. Single monopodial leafy stem, with flowers carried slightly above the leaf plane, inflorescences grow from the leaf axils.
- *Average height from base (plant grown in hanging basket, so no soil line present) to top of foliage*.—30.5 cm.
- *Average height from base (plant grown in hanging basket, so no soil line present) to top of flowers*.—51.3 cm.
- *Plant spread*.—Average of 46.2 cm.
- *Normal pot size*.—Hanging basket (8 by 8 cm, square).
- *Growth rate*.—Moderate.
- *Plant vigor*.—Moderate.
- *Propagation type*.—Meristematic tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility*.—Similar to other *Vanda* varieties.
- *Environmental tolerances*.—Adapt to, at least, USDA Zones 11 and 12 and temperatures as high as 40 degrees Celsius; high tolerance to rain; moderate to high tolerance to wind.

Root system:

- *General*.—Densely rooting; with aerial roots only.
- *Dimensions, mature roots*.—57.8 cm long with a diameter of 0.5 cm, on average.
- *Texture*.—Very fleshy; non-fibrous.
- *Color*.—Greyed-Green, near RHS 192A to 192C; root apex is yellow-green, RHS 146A.

Stem:

- *Branching habit*.—Monopodial; no lateral branches present.
- *Number of primary (main) stems per plant*.—One.
- *Number of secondary (lateral) branches per plant*.—None.
- *Appearance and shape*.—Circular, formed by the leaf sheaths.
- *Length*.—18.5 cm.
- *Diameter*.—0.9 cm.
- *Internode length*.—0.8 cm.
- *Luster*.—Matte.
- *Aspect*.—Near vertical.
- *Strength*.—Very strong.
- *Color, juvenile*.—Greyed-orange, near RHS 164B.
- *Color, mature*.—Greyed-orange, near RHS 164B.
- *Color at internodes*.—Yellow-green, near RHS 150D.
- *Pubescence*.—Glabrous.

Foliage:

- *Arrangement*.—Distichous.
- *Quantity*.—Approximately 22 leaves per plant.
- *Dimensions*.—19.5 cm long and 2.9 cm wide, on average.
- *Shape of blade*.—Ligulate; strongly carinate.
- *Aspect*.—Moderately curved.
- *Apex*.—Unequal praemorse.
- *Base*.—Sheathing.
- *Sheath dimensions*.—2.7 cm long and 1.3 cm wide, on average.
- *Sheath color*.—Yellow-green, near in between RHS 150C and 151D.
- *Margin*.—Entire.
- *Pubescence, texture and luster of adaxial surface*.—Glabrous, smooth, and matte.
- *Pubescence, texture and luster of abaxial surface*.—Glabrous, smooth, and matte.
- *Color*.—Juvenile foliage, adaxial surface — Green, near RHS 143C, and darker towards the margins, near 137C. Juvenile foliage, abaxial surface — Green, near RHS 143A to 143B. Mature foliage, adaxial surface — Green, near RHS 137B. Mature foliage, abaxial surface — Yellow-green, near RHS 144A.
- *Venation*.—Parallel.
- *Venation color, adaxial surface*.—Green, near RHS 137B.
- *Venation color, abaxial surface*.—Yellow-green RHS 144A.
- *Petiole*.—No petioles present, leaves sessile.

Inflorescence:

- *Inflorescence arrangement*.—Axially placed raceme.
- *Natural flowering season*.—Autumn into winter.
- *Time to flower*.—Approximately 10 months.

*Flowers per inflorescence*.—Average of 9; 8 open flowers and 1 bud.

*Inflorescence height*.—Approximately 24.0 cm (measured from base of lowest flower to top of upper flower).

*Inflorescence diameter*.—Approximately 17.4 cm.

*Peduncle*.—Dimensions — Approximately 39.6 cm long and 0.7 cm wide. Aspect — Approximately 30 degree angle to lateral branch axis. Strength — Moderately strong. Texture and luster — Glabrous and moderately glossy. Color — Yellow-green, near RHS 144A.

Bud:

*Length*.—Average of 2.0 cm.

*Diameter*.—Average of 1.8 cm.

*Shape*.—Broad obovate.

*Pubescence, texture and luster*.—Glabrous, smooth and moderately glossy.

*Color*.—Purple, near RHS N77B; base is yellow-green, near RHS 145A and 145B.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum; the two lateral petals slightly to moderately overlap the dorsal sepal and the lateral sepals; lateral sepals slightly overlapping; dorsal sepal is free of the lateral sepals.

*Aspect*.—Flowers are outward-facing to slightly nodding.

*Vertical height*.—Approximately 11.3 cm.

*Diameter*.—Approximately 10.7 cm.

*Depth*.—Approximately 3.7 cm.

*Fragrance*.—No fragrance.

*Lastingness*.—3 weeks.

*Persistent*.—Self-cleaning.

*Petals*.—Quantity of Petals — 3 unfused petals; two conventional petals and one labellum. Arrangement — One lateral petal on each side. Length — Approximately 5.5 cm. Width — Approximately 4.8 cm. Shape — Broad ovate to near orbicular. Apex — Obtuse. Base — Cuneate. Margin — Entire; moderately undulate. Pubescence, texture and luster of upper surface — Glabrous, velvety and matte. Pubescence, texture and luster of lower surface — Glabrous, velvety and matte. Color when opening, upper surface — Violet, near RHS N87B to N87C. Color when opening, lower surface — Purple-violet, near RHS N82D, and darker towards the margins, near RHS N82A to N82B. Color when fully opened, upper surface — Violet, near RHS N87D, and darker towards the margins, near RHS N87B to N87C, with irregular dark purple blurs centrally and towards the margins, nearest to RHS N87A, and distinct dark purple elongated spots at the base, RHS N87B. Color when fully opened, lower surface — Purple-violet, near RHS N82D, and violet towards the margins, near RHS N87B to N87C, with irregular dark purple blurs centrally and towards the margins, nearest to RHS N87A but lighter, and distinct dark purple elongated spots at the base, nearest to RHS N87B but lighter. Fading, upper surface — Not fading. Fading, lower surface — Not fading. Venation color, fully opened, upper surface — Violet, near RHS N87A; main vein is tinged purple-violet, RHS N82B. Venation color, fully opened, lower surface — Violet, near RHS N87B.

*Labellum*.—Shape — Three-lobed; the shape of the lateral lobes is broad ovate to rectangular and the aspect is involute; the central lobe is broad ovate to near rectangular and the aspect is revolute. Length — Central lobe — Approximately 1.9 cm. Lateral lobes — Approximately 0.8 cm. Width — Central lobe — Approximately 1.1 cm. Lateral lobes — Approximately 0.6 cm. Apex, central lobe — Emarginate. Apex, lateral lobe — Obtuse. Base, central and lateral lobes — Cuneate. Margin, central and lateral lobes — Entire; central lobe moderately undulate and lateral lobes not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Purple, near RHS 79A, to violet-blue, near RHS N92A. Lateral lobes — Greyed-white, near RHS 156D, and strongly tinged purple-violet, RHS N78D; dotted purple-violet, near RHS N81A, and violet at the base, near RHS N87A; upper margin yellow, near RHS 13B. Color when opening, lower surface — Central lobe — Violet, near RHS 83A, to violet-blue, near RHS N92A; lighter towards the base, RHS N87A. Lateral lobes — Greyed-white, near RHS 156D, and heavily tinged purple-violet, especially towards the margins, near RHS N81C to N81D. Color when fully opened, upper surface — Central lobe — Violet-blue, in between near RHS 79A and N92A. Lateral lobes — Greyed-white, near RHS 156D, and strongly tinged purple, RHS N78D; dotted purple-violet, near RHS N81A, and violet at the base, near RHS N87A; upper margin yellow, near RHS 13B. Color when fully opened, lower surface — Central lobe — Violet, near RHS 83A, to violet-blue, near RHS N92A; lighter towards the base, RHS N87A. Lateral lobes — Greyed-white, near RHS 156D, and heavily tinged purple-violet, especially towards the margins, near RHS N81C to N81D. Fading, upper surface — Not fading. Fading, lower surface — Not fading. Venation color, fully opened, upper surface — Central lobe — Violet, near RHS 79A, to violet-blue, near RHS N92A; lighter towards the base, RHS N87A. Lateral lobes — Greyed-white, near RHS 156D, and strongly tinged purple, RHS N78D; dotted purple-violet, near RHS N81A, and violet at the base, near RHS N87A; upper margin yellow, near RHS 13B. Venation color, fully opened, lower surface — Central lobe — Violet, near RHS 83A, to violet-blue, near RHS N92A; lighter towards the base, RHS N87A. Lateral lobes — Greyed-white, near RHS 156D, and heavily tinged purple-violet, especially towards the margins, near RHS N81C to N81D.

*Spurs*.—Quantity — Average of 1. Length — Approximately 0.7 cm. Diameter — Approximately 0.35 cm. Vertical height — Approximately 0.6 cm, at the base. Shape — Short triangular. Apex — Bluntly acute. Base — Broad Cuneate. Pubescence, texture and luster — Glabrous, smooth, and matte. Color — Greyed-purple, near RHS N187D, and striped violet, near N87C to N87D.

*Sepals*.—Quantity — Average of 3 unfused sepals. Arrangement — One dorsal sepal and two lateral sepals. Length — Dorsal sepal — Approximately 5.8 cm. Lateral sepals — Approximately 6.3 cm. Width — Dorsal sepal — Approximately 4.8 cm. Lateral sepals — Approximately 5.9 cm. Shape — Dorsal sepal — Broad ovate. Lateral sepals — Broad ovate. Apex, dorsal and lateral sepals — Obtuse. Base, dorsal and lateral sepals — Cuneate. Margin, dorsal and lateral sepals — Entire; dorsal sepals are slightly undulate and lateral sepals are moderately to highly undulate. Pubescence, texture and luster — Glabrous, velvety, and matte on both the upper and lower sepal surfaces. Color when opening, upper surface — Both dorsal and lateral sepals are violet, near RHS N87D, and darker towards the margins, near RHS N87B to N87C. Color when opening, lower surface — Both dorsal and lateral sepals are purple-violet, near RHS N82D, and darker towards the margins, near RHS N82A to N82B. Color when fully opened, upper surface — Both dorsal and lateral sepals are purple-violet, lighter than RHS N82D, and darker towards the margins, RHS N82B to N82C, with irregular tessellation centrally and towards the margins, nearest to RHS N87A, and distinct dark purple elongated spots at the base, RHS N87B. Color when fully opened, lower surface — Both dorsal and lateral sepals are purple-violet, lighter than RHS N82D, and darker towards the margins, RHS N82A to N82B, with irregular tessellation centrally and towards the margins, nearest to RHS N87A but lighter, and distinct dark purple elongated spots at the base, RHS N87B but lighter. Fading, upper surface — The color of all sepals does not fade. Fading, lower surface — The color of all sepals does not fade. Venation color, fully opened, upper surface — Both dorsal and lateral sepals are violet, near RHS N87A. Venation color, fully opened, lower surface — Both dorsal and lateral sepals are violet, near RHS N87B.

*Pedicels*.—Length — Approximately 6.1 cm. Diameter — Approximately 0.5 cm. Angle — Approximately 75 degree angle to peduncle axis. Strength — Moderate. Texture — Glabrous, axially angled with 5 "ribs", axially twisted (due to resupination) Luster — Glossy. Color — Purple, near RHS 76C, and fading to purple, near RHS 76A, to violet, RHS 84C, towards the distal end.

*Bract*.—Quantity — One bract present at the base of each pedicel. Shape — Reniform; folded around the base of each pedicel. Dimensions — Average of 1.5 cm long and 1.5 cm wide. Apex — Broad acute. Base — Broad Cuneate. Margins — Entire. Color, both surfaces — Yellow-green, near RHS 145A.

Reproductive organs:

*Column*.—Length — Approximately 0.55 cm. Diameter — Approximately 0.7 cm. Color — White RHS 155B.

*Ovary*.—Position — Inferior. Diameter — Approximately 0.2 cm. Color — Purple, near RHS 76A, to violet towards the distal end, near RHS 84C.

*Pollinia color*.—Yellow-orange RHS 17C.

Seed and fruit: No fruit and seed production has been detected to date.

COMPARISONS WITH THE PARENT PLANTS

Plants of the new cultivar 'SPCDW1409' are similar to the seed parent, *Vanda* 'F211', in most horticultural characteristics. However 'SPCDW1409' differs from the seed parent in the following characteristics:

1. The inflorescence of 'SPCDW1409' is shorter than the inflorescence of 'F211'.
2. The flower color of 'SPCDW1409' is a vivid violet, whereas the flower color of 'F211' is a dull violet.
3. 'SPCDW1409' exhibits a slower growth rate when compared to 'F211'.

Plants of the new cultivar 'SPCDW1409' are similar to the pollen parent, *Vanda* 'JBL211', in most horticultural characteristics. However 'SPCDW1409' differs from the pollen parent in the following characteristics:

1. The inflorescence of 'SPCDW1409' is taller than the inflorescence of 'JBL211'.
2. The flowers of 'SPCDW1409' are smaller than the flowers of 'JBL211'.
3. The flowers of 'SPCDW1409' exhibit a generally violet color, whereas the flowers of 'JBL211' exhibit a generally cerise to red color.
4. 'SPCDW1409' exhibits a faster growth rate when compared to 'JBL211'.

COMPARISON WITH THE MOST SIMILAR *VANDA* CULTIVAR KNOWN TO THE INVENTOR

A comparison of 'SPCDW1409' with the most similar *Vanda* cultivar known to the inventor, *Vanda* 'SPCDW1404' (U.S. patent application Ser. No. 14/757,055; Community Plant Variety Rights application number 2014/2941), is described in Chart 1.

CHART 1

| Characteristic | 'SPCDW1409' | 'SPCDW1404' |
|---|---|---|
| Size of Flower Petals | Smaller than those of 'SPCDW1404'. | Larger than those of 'SPCDW1409'. |
| Flower Petal Arrangement | Higher degree of sepal overlap compared to 'SPCDW1404'. | Lesser degree of sepal overlap compared to 'SPCDW1409'. |
| Position of Flower Petals in Relation to Dorsal Sepal | Petals exhibit more forward tilt, in relation to the dorsal sepal. | Petals exhibit less forward tilt, in relation to the dorsal sepal. |
| General Coloration of the Flower. | Light violet with darker violet tessellation. | White and tinged violet-blue towards the apex; moderately dotted with dark purple. |
| Tessellation of the Flower | Some tessellation is visible. | No clear tessellation. |
| General Coloration of the Labellum | Lateral lobes are greyed-white and strongly tinged purple; dotted purple-violet and violet at the base; upper margins are yellow. Central lobe is purple to violet-blue. | Lateral lobes are purple and striped violet at the base, with a yellow-orange dot at the base. Central lobe is violet-blue. |

That which is claimed is:

1. A new and distinct variety of *Vanda* plant named 'SPCDW1409', substantially as described and illustrated herein.

* * * * *